United States Patent [19]

Mehl

[11] 4,174,713
[45] Nov. 20, 1979

[54] DEVICE FOR PERMANENT REMOVAL OF HAIR

[76] Inventor: Thomas L. Mehl, 5821 Cypress Rd., Plantation, Fla. 33317

[21] Appl. No.: 837,172

[22] Filed: Sep. 28, 1977

Related U.S. Application Data

[63] Continuation-in-part of Ser. No. 670,682, Mar. 26, 1976, abandoned.

[51] Int. Cl.$^2$ .............................................. A61N 3/04
[52] U.S. Cl. ............................ 128/303.13; 128/303.17
[58] Field of Search ................. 128/303.13, 354, 303.1, 128/303.14, 303.15, 303.16, 303.17, 303.18; 219/90, 233, 234

[56] References Cited

U.S. PATENT DOCUMENTS

| | | | |
|---|---|---|---|
| 1,071,978 | 9/1913 | White | 128/303.13 |
| 2,249,894 | 7/1941 | Goldenstein | 128/303.13 |
| 2,417,530 | 3/1947 | Weiser | 128/303.13 X |
| 2,477,467 | 7/1949 | Rose | 219/234 |
| 2,700,975 | 2/1955 | Hopfinger et al. | 128/303.15 |
| 2,888,927 | 6/1959 | Fozard | 128/303.13 |
| 3,831,607 | 8/1974 | Lindemann | 128/303.17 |
| 3,916,909 | 11/1975 | Kletschka et al. | 128/354 |
| 3,999,552 | 12/1976 | Huggins | 128/303.13 |
| 4,033,350 | 7/1977 | Hashi | 128/303.13 |
| 4,041,952 | 8/1977 | Morrison, Jr. et al. | 128/303.13 |

FOREIGN PATENT DOCUMENTS

138672  8/1961  U.S.S.R. ............................. 128/303.17

*Primary Examiner*—Lee S. Cohen
*Attorney, Agent, or Firm*—Shlesinger, Arkwright, Garvey & Dinsmore

[57] ABSTRACT

Hair is permanently removed by applying concentrated high frequency waves to a hair very close but slightly spaced from the skin with a device which induces conduction along the internal section (medulla) of the hair shaft and downwardly to the matrix area to bring about permanent damage to the matrix area and release of the hair.

41 Claims, 13 Drawing Figures

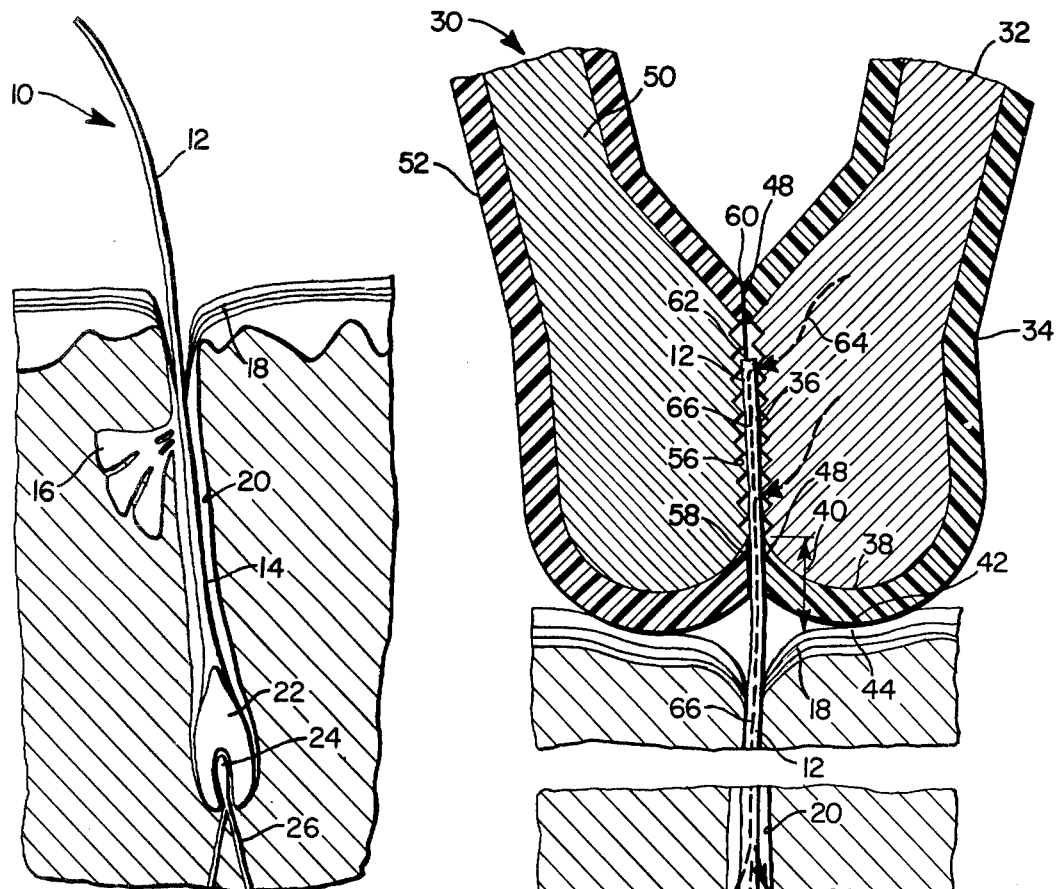
FIGURE 1
FIGURE 2
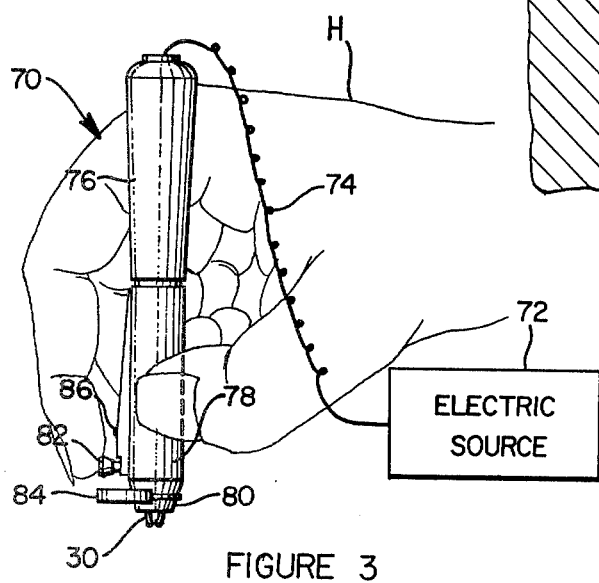
FIGURE 3

DEVICE FOR PERMANENT REMOVAL OF HAIR

This application is a continuation-in-part of my copending application Ser. No. 670,682, filed Mar. 26, 1976, entitled Epilation Device, now abandoned.

BACKGROUND OF INVENTION

This invention relates to a device for effecting removal of hair and permanent impairment of future hair growth.

Many different types of devices have been used in an effort to permanently remove unwanted hair. Most of the more recently developed devices use high frequency electricity in an effort to destroy the papilla area at the base of the hair shaft.

One of the techniques in use for many years employs a needle which is to be inserted into the follicle adjacent the hair in an effort to reach the papilla area. High frequency electrical waves are then applied to the needle in an effort to destroy the hair producing papilla area. The more generally used type of such devices has a needle which is used in combination with a tweezer. These types of devices are illustrated in U.S. Pat. Nos. 3,054,405, 2,894,512, and 853,096. The drawback of these devices is that the insertion of the needle under the skin produces irritation and swelling, and burning of the tissues.

More recently, there has been general use of a hair removal device using an electrically charged tweezer which grips the hair a considerable distance from the skin and to which high frequency electrical waves are directly applied. Such devices are shown in U.S. Pat. Nos. 2,888,927, 2,417,530, and 1,071,978. Since there is no requirement for insertion of a needle into the skin, soreness and irritation of tissue is eliminated. However, this type of device requires more time for hair removal, does not effectively kill hair regrowth capability, and in many cases has resulted in severe skin burns when the tweezer tip is brought too close to the skin surface.

In addition to these drawbacks, neither of the above types of device can be used in small and inaccessible sensitive areas, such as the nostril or ear, without risk of severe pain, or burning of tissue.

SUMMARY AND FEATURES OF THE INVENTION

This invention overcomes all of the aforementioned difficulties of the prior art devices.

It further provides a readily usable instrument which obviates the difficulties of operation encountered with the previously used devices.

A feature of this invention is the successful use of the central section of the hair (medulla) to provide an electrical path from the device directly to the matrix area and to the papilla to assure sufficient damage of the tissue and cells of the matrix area to preclude future hair regrowth.

Another feature of this invention is a special hair removal device which can readily be used by an unskilled and untrained person with excellent results.

A further feature of this invention is a new method of hair removal which is performed at a much faster rate than heretofore, is painless, and does not burn or irritate the skin surface or underlying tissues.

An additional feature of this invention is the provision of apparatus and method which can easily be used to remove hair in difficult and inaccessible area, such as the nose or ear.

A still further feature of this invention is a special hair grasping assembly which applies high frequency electrical energy waves to a hair at a point and in an amount sufficient to induce conduction through the hair medulla section so as to assure matrix damage without arcing to or burning of the skin.

Another feature of this invention is the provision of a readily operable device in which both the hair grasping and electrical application are effected substantially simultaneously.

A yet additional feature of this invention is a preparation technique which substantially reduces the time required to effectively remove the hair.

A still further feature of this invention is to provide a hair grasping assembly particularly constructed to focus and isolate high frequency energy waves at the contact area with the hair to substantially increase electrical conductivity between the assembly and the interior of the hair shaft.

A yet further feature of the invention is to provide a hair grasping assembly construction which permits the area of application of the high frequency energy waves to the hair very close to the skin but will prevent burning.

A still further feature of the invention is the provision of a hand-held hair removal device in which the hair grasping elements are differently and specially configured and are readily substitutable.

DESCRIPTION OF THE DRAWINGS

FIG. 1 shows a cross-sectional view of a section of tissue showing a hair and the several parts associated therewith.

FIG. 2 is a sectional view enlarged and partially cut away of the hair of FIG. 1 showing in section the grasping elements of the invention in position about the hair.

FIG. 3 is a plan view of the hair removal device.

DESCRIPTION OF THE INVENTION

Figure 4:
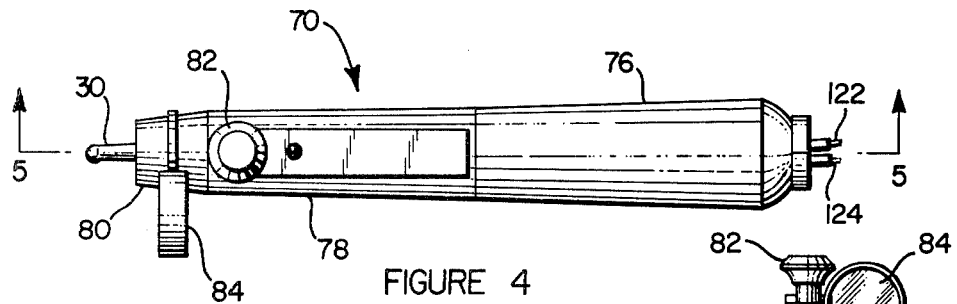
FIG. 4 is a top view of the hair removal device shown in FIG. 3.

Referring particularly to FIGS. 1 and 2, a hair generally indicated at 10 has an upper portion 12 which extends up above the skin surface and tissue area, and an interior lower shaft portion 14 extending beneath the skin surface which passes adjacent oil glands 16 disposed immediately below the epidermis area 18. The hair section 14 is connected to an external sheath layer 20.

The growing area for the hair is located in the matrix area generally indicated at 22. This contains the papilla 24 which is supplied with nutrients through the blood vessel 26. It is this matrix area that must be reached and destroyed by electrical energy if future hair growth is to be prevented, inasmuch as all of the tissue in the hair above this area is dead fibrous material.

The hair shaft, including sections 12 and 14, is composed primarily of horny, fibrous cells that have coalesced. Externally, the fibrous substance is covered by a delicate layer of scales which form an outer cuticle surface which engages the sheath 20. The center of the shaft is occupied by an axially extending medulla which is composed of angular cells grouped along the central axis of the hair as a core. This cell structure contains several elements, one of which is iron. Although the medulla is not a good conductor in the normal sense, this medulla section is a better conductor than the outer peripheral cellular structure of the hair. The target for the electrical current is the papilla 24, the matrix 22 and the adjacent cellular structure 28 immediately thereabove at the base of the lower portion of the hair shaft 14, as indicated by dotted arrows in FIG. 2.

Referring particularly to FIG. 2, the free ends of a tweezer generally indicated at 30 are shown in position grasping the hair 12.

The arm 32 shown in the right has an insulative coating 34 and a planar and ridged hair engaging surface 36. It should be noted that the lowermost portion 38 of the arm 32 is disposed below the lowermost section of the hair engaging surface or pad 36. This rearward displacement of the bottom portion of the hair engaging surface 36 is essential for successful operation of the unit in that there must be a sufficient distance 40 between the lowermost section of the hair engaging surface 36 and the surface of the skin 44. The thickness of the insulative layer 34 between the tip 38 and the outer surface 42 of the insulative coating is also to be considered as part of the dimension 40. This dimension is approximately one millimeter in usual practice.

The non-conductive insulative layer surrounds the flat hair engaging conductive surface or pad 36 and extends around and flush thereto as indicated at 48. To be effective, it must be high frequency insulative material, such as that used on RF cable. Teflon is an example of a very good high frequency insulative material.

The other arm 50 of the tweezer is of generally the same construction as arm 32, and has an insulative layer 52, a lower skin engaging surface 44, and a flat conductive surface having an uneven or toothlike surface 56 similar to that shown for the hair engaging surface 36 of arm 32.

The insulative layer extends around the hair engaging surface as respectively shown at 58 and 60 and meets with the insulative surfaces of arms 32 to effect a closed sealed area therebetween.

It will be observed that the hair 12 is shortened as indicated at 62. It has been found that substantially better results are obtained when the hair is short, or has been cut, and particularly where the hair itself is enclosed by the hair engaging surfaces.

It has been found that the high frequency electrical waves traveling along arm 32 which is made of metal (shown at 64), penetrate to the interior of the hair shaft 12 and extend down the central medulla section as shown by the dotted line 66 and lines 68 to the areas adjacent the base of the hair shaft 28, the matrix 22 and the papilla 24, resulting in thermal damage to the cells of these areas as well as cauterizing of the vein 26 to destroy any further hair propagating capability.

This apparently is made possible by a focusing effect which is produced by the relatively small area (substantially less than one three hundredth of an inch) of the hair engaging surfaces, and the closed insulative arrangement which substantially cuts high frequency energy wave losses. Both of these factors apparently materially assist in having the electrical waves penetrate to the interior central portion of the hair which is a better conductor than the exterior portion, and which acts as a conductor leading directly to the papilla. This contrasts sharply with the prior devices in which the energy waves traveled along the external portion of the hair and stood very little chance of reaching the papilla.

The shortness of the hair and the relatively close point at which electric wave energy is applied to the hair have been found to also be important factors. Apparently, the short hair reduces radiation losses, while the closeness of application to the skin, such as a dimension 40 apparently reduce the internal resistance to energy wave travel along the medulla a substantial amount.

The device of the instant invention is generally indicated in FIG. 3, and more particularly shown in FIGS. 4 through 7.

Referring particularly to FIG. 3, the device generally indicated at 70 is held in the hand as shown. It is approximately the length of the hand, and preferably has a sectional width approximately equal to the width of the finger or less. It is connected to an electrical source 72 of high frequency electrical waves through a coaxial cable 74. The casing is made of insulative material such as nylon, or any other non-conductive material, and has upper and lower sections 76 and 78, respectively. The lower portion 78 of the casing has a nose 80 through which the tweezer tips, generally indicated at 30, project. The nose is held in position internally within the housing by the flanges 81.

A button 82, pressible by a fingertip, as shown in FIG. 3, closes the tweezer and simultaneously activates the electrical circuit switch and the on-off timing light 86. When it is depressed, it also engages the switch assembly to electrically connect the hair engaging surfaces of the tweezer tips 30 with the high frequency energy waves which are conducted through the coaxial cable 74 from the electric source 72. The magnifying lens 84 is provided to assist in more rapid and accurate grasping of hairs during the course of operation.

Figure 5:
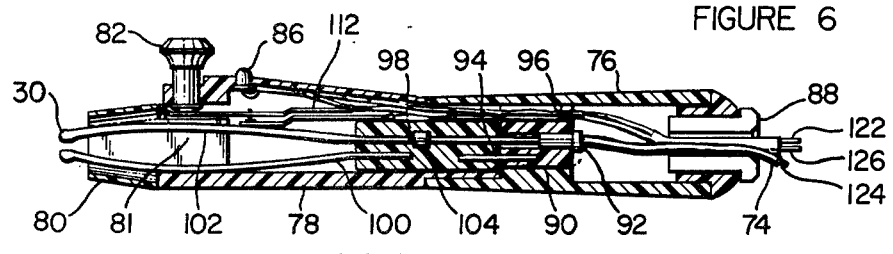
FIG. 5 is a cross-sectional view of the hair removal instrument along line 5—5 of FIG. 4.

A cross-sectional view of the hair removal device 70 is shown in FIG. 5 and illustrates the mechanical and electrical interconnection of the elements.

The upper and lower casing elements 76 and 78 are made of plastic or any non-conductive material and are cylindrical hollow elements that are interfitted and readily disconnectable. Tapered removable end piece 80 is disposed at the forward end of housing 78, and is hollow to permit the tweezer ends 30 to project therethrough. The tweezer ends 30 are brought together by depression of the button 82 which also turns on the light 86 mounted directly behind it.

Power is supplied through the rear of the unit and the plastic grommet 88 through a two wire conductor and the coaxial cable 74. A support and terminal receiving socket 90 has at its front face the two axial passages. One extends through the socket and supports pin receiving member 92. The second receives alignment pin 94. A third axial passage 96 permits the two control voltage wires to pass therethrough and to the switch assembly disposed immediately behind the button 82.

An electrical tweezer plug 98 which receives the lower tweezer arm 100 and the upper tweezer arm 102 fits within the casing 76 and has a pin 104 that extends out and into engagement with the pin receiving member 92 of socket 90. Both the terminal receiving socket 90 and the tweezer plug 98 are made of high frequency insulative material.

It should be noted that with the removal of the forward nose section 80 of the casing, the forward interior section of the casing is exposed, permitting the ready removal of the tweezer and the socket plug by merely pulling on the ends of the tweezers 30 to disconnect the pins from the terminal receiving socket 90. A new tweezer with a different configured end section 30 but with an identical tweezer plug 98 can then be inserted quickly into the terminal receiving socket 90. The nose piece 80 has two side internal surface engaging pieces 81 which hold it in position. They are disposed beside the tweezers so as not to interfere therewith and permit the unit with the new set of tweezers to be operated immediately.

Figure 6:
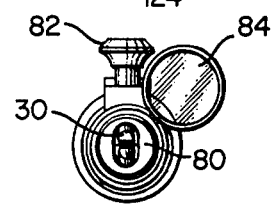
FIG. 6 is an end view of FIG. 4.

FIG. 6 shows an end view of the hair removing device of FIG. 4 looking directly at the end piece 80 through which the tweezer ends 30 project. It will be noted that there is ample space for different types of tweezer ends at the annular end of the casing 78. Further, it will be noted that the magnifying lens 84 is disposed adjacent the tip of the tweezers such that a good angled view of the hair and skin area immediately under the tweezer can be obtained.

Figure 7:
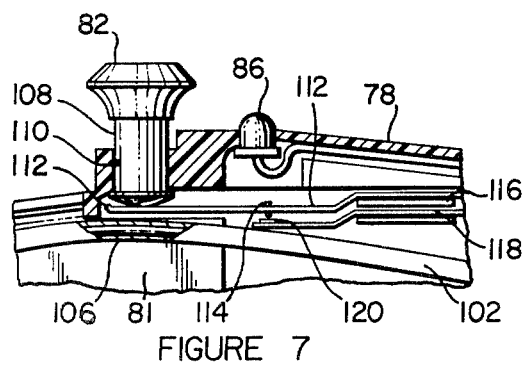
FIG. 7 is an enlarged fragmentary sectional view of FIG. 5 showing the switch and light assembly.

FIG. 7 shows an enlarged portion of the switch area of FIG. 5. The switch assembly is disposed immediately adjacent and close to the upper arcuate section of the upper tweezer arm 102 which is broken away at 106 to disclose an inner metallic member and the exterior insulative coating which extends the entire length of the tweezers.

The button 82 has a lower cylindrical section 108 which is slidably received within the passage 110 of the lower housing 78. A metallic leaf spring 112 extends over and below the bottom of the button 82 and is maintained in slight spring-like engagement with respect to it. It has a contact 114, and is seated at its other end within plastic receiving slot 116 of the housing. The lower leaf spring 118 is similarly supported and extends outwardly toward the bottom and has a contact 120 disposed immediately below and spaced from the contact 114.

Figure 8:
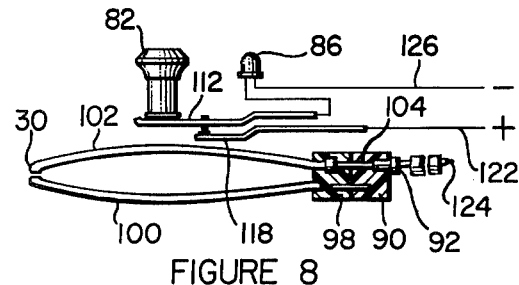
FIG. 8 is a diagrammatic schematic of the electrical and switch circuitry of the hair removal device.

The schematic drawing shown in FIG. 8 illustrates the operation and electrical arrangement of the unit. A control voltage is applied to line 122 which is connected to the leaf spring 118. On depression of the button 82, the leaf spring 112 is pressed downwardly to close the electrical contact, as well as to make contact with the upper tweezer arm. When the contacts 114 and 120 are closed (FIG. 7), the electrical signal travels through arm 112 and to the bulb 86 which is connected through line 126 to the electrical source. Either line 126 or a separate line connected to leaf spring 112 is connected to a control circuit in electrical source 72. This control circuit supplies high frequency energy waves to pin 92 through coaxial cable 74.

The pin 104 is directly connected to the upper arm 102 of the tweezers. When the two ends of the tweezers are brought together by depression of the button, electrical voltage is supplied through the upper arm to the hair which is grasped between them, as shown in FIG. 2. The upper arm is used to conduct the high frequency electrical waves as a safety factor, since the tip of the lower arm repeatedly comes in contact with the skin. In case of a break in insulation or electrical leakage, the possibility of a burn is precluded.

FIGS. 9 through 12 show various types of tips for the tweezer.

Figure 9:
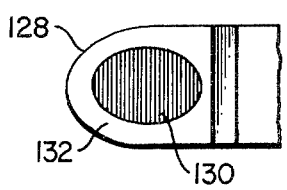
FIG. 9 is a plan view of the tip of the hair-grasping element of the hair removal device having an oval configuration.

FIG. 9 shows the oval type of configuration that is most frequently used. It has a generally oval tip 128 and a planar flat hair engaging surface 130. This tip corresponds to the tips shown in FIG. 2. Note the insulative surface completely surrounds the planar area 130 and is set back on all sides, as well as along the outermost tip area, as indicated at 132. The ridges on hair engaging surface 130 are very pronounced in this figure, but it should be noted that the drawing is many times actual size. The width of the hair engaging area is preferably no more than approximately one-sixteenth of an inch in width and no longer than an eighth of an inch. A range of acceptable cross-sectional area will depend upon use, frequency and other factors, but for the most part it is preferred that such area be approximately from one one-hundredth to one two-hundredths of an inch, with approximately one five-hundredths of an inch being a minimum. The gridded surface can be produced by a very fine file or coarse sandpaper. To the eye they appear as very small scratches.

The use of a grid surface has been found to increase the conductive capability and to reduce the time required to thermally damage the papilla area. The roughened ridged area presses into the hair and gives a better conductive path to the internal medulla section of the hair shaft.

Figure 10:
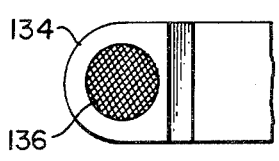
FIG. 10 is a plan view of another form of the tip of the hair grasping element having a circular grasping element.

FIG. 10 shows a rounded tip 134 which has a round pad 136. It will be noted in this figure that the contact surface 136 has crossed ridges.

Figure 11:
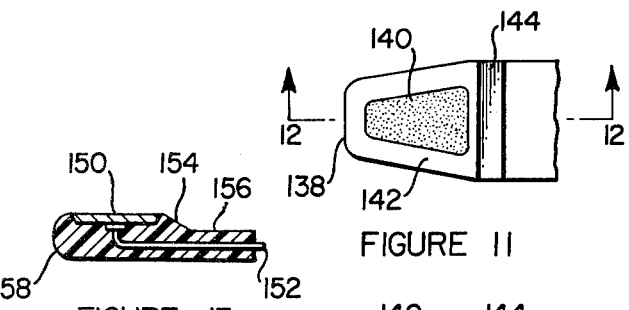
FIG. 11 is a plan view of still another tip configuration of the grasping element of the hair removal device.

FIG. 11 illustrates a tapered rectangular type of tip 138 with a tapered hair engaging section 140. This illustrates another type of roughened surface, of which it can be appreciated there will and possibly can be variations. This figure shows a type of small roughened beaded metal surface, similar to that of sandpaper. The peripheral surface 142 gives sufficient clearance between the outer periphery 140 and the edge of the tip to preclude burning.

Figure 12:
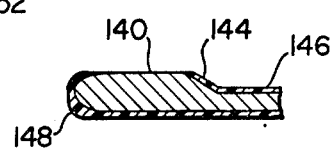
FIG. 12 is a cross-sectional view of FIG. 11.

FIG. 12 is a section along line 12—12 of FIG. 11. The sloping portion 144 tapers down to the arm proper as illustrated. The insulation covers the entire arm of the tweezer so that no radiation escapes therefrom except at the hair engaging surface 140. The insulation is flush with the hair engaging surface 140 and is discussed with respect to the tweezer end 30 of FIG. 2, and wraps continuously around the tip as shown at 148 and continues on back the arm, as shown.

Figure 13:
FIG. 13 is a cross-sectional view of another type of tip construction.

FIG. 13 shows a cross section of another type of tweezer end having a plastic arm usually made of high frequency non-conductive material, and a pad 150 to which the conductor 152 is connected to bring the high frequency energy waves thereto. The surface of the tweezer arm 156 has a raised section 154 and a blunted and rounded tip 158.

OPERATION

The hair removal device is preferably used after the hairs to be removed are cut to a preferable short length.

It has been found that reduction of the length of the hair substantially increases the capability of the unit and reduces the time required to effect hair removal. The preferable length for hair is from approximately one-sixteenth to three-sixteenths of an inch. It has been found that one effective way to pre-cut these hairs to the desired length is to shave the surface and then to wait two to three days for hair to attain the desired length. At that time, the length of the hair will be approximately that shown in FIG. 2. At this length, the hair is sufficiently long to be grasped by the tweezers and held in position between the hair engaging surfaces and also will be fully enclosed within the area between the two hair engaging pads, as also shown in FIG. 2. It has been found that when the shorter hair is completely contained within and between the two hair engaging surfaces there is no radiation of the electrical energy, and the length is sufficiently short to provide a reduced resistive path between that and the electrical ground in the matrix and papilla area.

FIG. 3 shows the tweezer in an upright position as it would be used substantially perpendicular to the skin, or possibly held at a slight angle.

The operator presses down against the skin with the tweezer ends to produce a depression in the skin around the hair, and then presses the button 82 to bring the tweezer ends 30 into engagement with the hair and to close the insulative sections around the entire hair engaging area formed by the two opposed flat surfaces, as shown in FIG. 2.

Simultaneously with the pressing of the button 82 the switch assembly closes and connects high frequency electrical waves to the arm 32 of FIG. 2 which then flows through the hair engaging surface 36 and into the portion of the hair above the skin.

It should be noted that the dimension 40 of FIG. 2 discussed above is critical and that either arcing or radiation is prevented because of the gap between the skin surface and the lower portion of the hair engaging surface and the insulation which folds around and rearwardly from the outer extremity of the tip of the tweezer to the hair engaging surfaces. A voltage of from 100 to 600 volts can be used without causing burning or arcing. Prior devices have been unable to safely operate above approximately 250 volts.

In operation, the tweezer is held against the skin for the duration of time required for the hair to release. In this respect it is very important to note that the hair is not pulled, but that the tweezer is held in continuous position for the time interval required to completely thermally damage the matrix area.

In the previously used tweezer devices biopsies have shown that the current does not travel down the interior portion (medula) of the hair but along the outside of it and burns the area immediately under the skin surface, usually not penetrating down as far as the oil gland 16 of FIG. 1. With the instant device the internal travel of the high frequency electrical waves through the medulla brings it down to the papilla in every instance, and holding the tweezer in position, as shown, will permit complete thermal destruction of the matrix area. There is no thermal damage along the upper portion of the hair shaft. The tweezer is not removed until the hair itself has disengaged from the matrix area and has released. The hair will pop up on release. This interval will vary, but it has been found that with complete disintegration of the hair in the matrix area, the hair will release. That is, the hair will very slightly pop up and come out of its own accord. The operator waits for this to occur before removing the tweezer from the skin surface with the hair between its hair engaging pads.

It has been found that the device and method work without either irritation or burning, and it removes hair permanently, as contrasted with the prior devices which do not do so. A hair, depending upon its characteristic type can be removed in two to twenty seconds, with most hairs being removed within less than ten seconds. This time is substantially less than that for the other types of tweezer devices. Permanent damage is assured to the papilla of the hair in each instance, contrary to the experience with the prior devices. The use of the medulla section as a conductive path taking the high frequency directly to the matrix area produces thermal damage of such a magnitude that further hair growth is precluded. Biopsies have shown that the entire cellular structure in the matrix including the bottom area of the hair shaft, is in effect released, the papilla, and even the blood vessels, are thermally damaged.

This is possible because of the effective concentration of high frequency across the hair at a point close to the skin. To do this, it is essential that the point of application be remote from the periphery of the device and that it be shielded by the use of high frequency insulative material. Ordinary electrical insulation is not adequate. Further, the dimension must be such that there is no leakage to the skin to cause a burn. This will determine the distance 40 of FIG. 2, which has been found to be approximately one thirty-second of an inch.

The focusing of the high frequency waves which can be anywhere from one to a thousand megahertz enables them to reach the medulla section and to travel downwardly through the hair shaft. Also because of the insulation, radiation losses are minimized.

The point of application of the high frequency energy waves, is also important, and the insulation of the hair engaging surfaces permits them to be applied at a point closer to the skin without the danger of arcing as experienced in prior tweezer devices. These devices were required to be kept away from the skin surface a substantial distance, ranging from one-eighth to three-sixteenths of an inch. In contrast, the instant device permits the high frequency energy to be applied at a distance of and preferably no more than one thirty-second of an inch. This closeness contributes substantially to the effectiveness of the device.

The insulated tip also permits the operator to readily engage the hair at this close distance, because the tip can be rested against the skin itself without danger of producing a burn. This has not been possible in any of the previous devices, including those that did have some insulation.

The tips of the arms should be unpointed to minimize the arcing tendency. The prior devices, failing to recognize this, have tapered the arm down to a point, with the consequent result that they did encounter a substantial arcing and burning problem.

The location of the hair engaging surface, the construction of the tip of the arm, and the type of insulation keep the high frequency energy waves from moving to the skin surface.

These elements are missing from the prior type of tweezer constructions.

Further, if the arm does have a pointed configuration in any plane, it makes it extremely difficult to apply effective insulation of the required thickness, or of such construction that it will maintain a closed contact with the opposing arm.

The effectiveness of the instant device is also increased by the use of smaller hair engaging surfaces than previously used. This is believed due to the further concentration or focusing of high frequency waves at the point of contact with the hair. The area of the hair engaging surfaces are preferably at least one-half that of previous devices.

It should also be noted that the periphery of the hair engaging surface itself, particularly along the lower periphery nearest the skin surface, should be unpointed, and either rounded or flat. It has been found that a somewhat pointed configuration will require a greater thickness of insulative material between it and the skin to prevent arcing or burning, as well as increasing the distance which ordinarily is held at one thirty-second of an inch.

The surfaces of the hair engaging surfaces themselves are also important. It has been found that the effectiveness of them have been increased substantially by roughening the surface which either due to better grasping or possibly even closely pressing through the outer scaler surface of the hair assists the high frequency waves in reaching the relatively better conductor medulla section of the hair.

Another factor increasing effectiveness of the unit is the cutting of the hair shaft itself relatively close to the skin as shown in FIG. 2. Where the hair is of such reduced length, less radiation escapes along the portion of the hair shaft above the hair engaging surfaces, permitting greater amounts of high frequency waves to travel downwardly to the matrix.

Accordingly, the instant invention involves a new type of device used for hair removal and which employs high frequency electrical waves which travel along the medulla to produce permanent damage to the hair matrix. This is effectively accomplished without any type of discomfort to the user or any risk of skin tissue burn or discoloration. In addition, the hair is permanently removed in one treatment. Other previously used devices require multiple treatment to kill one matrix or papilla area.

While this invention has been described in connection with different embodiments thereof, it will be understood that it is capable of further modification, and this application is intended to cover any variations, uses, or adaptations of the invention following, in general, the principles of the invention and including such departures from the present disclosure as come within know or customary practice in the art to which the invention pertains, and as may be applied to the essential features hereinbefore set forth and fall within the scope of the invention or the limits of the appended claims.

What is claimed is:

1. A hair removal device, comprising:
   (a) two opposed relatively movable support members having lower end sections which are in position to engage each other
   (b) each of the end sections having a substantially flat hair engaging surface adjacent and spaced from the periphery thereof
   (c) at least one of the hair engaging surfaces being made of conductive material
   (d) a high frequency energy wave source which is electrically connected to said one conductive hair engaging surface, and
   (e) high frequency electrical wave insulative material bordering each of the hair engaging surfaces and disposed between the periphery thereof and the periphery of the end section which is of sufficient thickness to restrict lateral radiation from the hair engaging surfaces outwardly to the periphery of the end sections.

2. The hair removal device as set forth in claim 1, wherein:
   (a) the high frequency electrical wave insulation completely surrounds the hair engaging surfaces and is substantially flush therewith.

3. The hair removal device as set forth in claim 2, wherein:
   (a) the distance between the periphery of the hair engaging surfaces and the periphery of the lower section of the movable support members is approximately one thirty-second of an inch.

4. The hair removal device as set forth in claim 1, wherein:
   (a) the distance between the periphery of the hair engaging surfaces and the periphery of the lower section of the movable support members is approximately one thirty-second of an inch.

5. The hair removal device as set forth in claim 1, wherein:
   (a) the two opposed relatively movable support members are slender elongated arms, the outer surfaces of which are high frequency electrical wave insulating material.

6. The hair removal device as set forth in claim 5, wherein:
   (a) the distance between the periphery of the hair engaging surfaces and the periphery of the lower section of the movable support members is approximately one thirty-second of an inch.

7. The hair removal device as set forth in claim 5, wherein:
   (a) the area of the hair engaging surfaces is between one-fiftieth to one five-hundredth of an inch.

8. The hair removal device as set forth in claim 1, wherein:
   (a) the area of the hair engaging surfaces is between one-fiftieth to one five-hundredth of an inch.

9. The hair removal device as set forth in claim 1, wherein
   (a) the shape of the lowermost periphery of the support sections preclude arcing to the skin.

10. The hair removal device as set forth in claim 1, wherein:
    (a) each of the hair engaging surfaces have a fine roughened surface.

11. The hair removal device as set forth in claim 1, wherein:
    (a) the lowermost periphery of at least one of the support sections is shaped to preclude arcing to the skin.

12. The hair removal device as set forth in claim 11, wherein:
    (a) each of the hair engaging surfaces have a fine rough surface.

13. The hair removal device as set forth in claim 11, wherein:
    (a) the hair engaging surfaces are approximately one-sixteenth of an inch wide and one-eighth of an inch long.

14. The hair removal device as set forth in claim 1, wherein:

(a) the relatively movable support members are mounted on an elongated hand-held housing of electrically insulative material and project outwardly from an end thereof.

15. The hair removal device as set forth in claim 14, wherein:
(a) a small finger actuated button is disposed adjacent the end of the hand-held housing and is mechanically connected to one of the relatively movable members for actuation thereof.

16. The hair removal device as set forth in claim 15, wherein:
(a) the housing contains electrical switch means for controlling application of high frequency energy waves to the hair engaging surface.

17. The hair removal device as set forth in claim 16, wherein:
(a) the button is mechanically interengageable with the switch means for actuation thereof.

18. The hair removal device of claim 17, wherein:
(a) the housing includes an electrical socket assembly and the relatively movable member having the conductive hair engaging surface is connected to the electrical socket assembly which permits its ready removal from the elongated housing.

19. The hair removal device of claim 17, wherein:
(a) the relatively movable support member having the conductive hair engaging surface has a conductive path along which the high frequency energy waves are conducted and which is insulated with a high frequency insulative material.

20. A hair removal device comprising:
(a) a hollow elongated hand-held housing of electrically insulative material approximately the length of a hand and the cross-sectional width of a finger
(b) at least one slender arm having an end portion which extends outwardly from a front end of the housing to engage the skin
(c) a first hair engaging surface mounted on, adjacent and close to but spaced from the outer periphery of the end portion of the arm
(d) a second hair engaging surface supported on the housing in opposed relatively movable position with respect to the first hair engaging surface such that the hair engaging surfaces can firmly grasp a hair between them and make good face-to-face contact
(e) at least one of the hair engaging surfaces being electrically conductive
(f) a high frequency energy wave source connected to one of the hair engaging surface, and
(g) high frequency energy wave insulative material disposed about the periphery of said at least one of the hair engaging surfaces to restrict radiation therefrom to the skin.

21. The hair removal device as set forth in claim 20, wherein:
(a) the arm is approximately one-eighth of an inch in width.

22. The hair removal device as set forth in claim 20, wherein:
(a) the surface of the arm is a high frequency energy wave insulative material.

23. The hair removal device as set forth in claim 20, wherein:
(a) the lowermost portion of the hair engaging surface connected to the high frequency energy wave source is spaced from the skin engaging surface approximately one thirty-second of an inch.

24. The hair removal device as set forth in claim 20, wherein:
(a) the housing has a forward section which is a removable nose section, removal of which provides access to the interior of the housing.

25. The hair removal device as set forth in claim 20, wherein:
(a) readily operable switch means is disposed on the housing adjacent the forward section thereof to control connection of the high frequency energy wave source with the hair engaging surface.

26. The hair removal device as set forth in claim 25, wherein:
(a) the switch means includes a button readily depressible by the finger of the operator and which is also connected to move the arm and bring the hair engaging surfaces into engagement with each other.

27. The hair removal device of claim 20, wherein:
(a) the arm is of substantial length and extends rearwardly into the housing a substantial distance to a support element which provides its sole fixed support, and
(b) the arm is readily yieldable to allow movement of its end portion toward the second hair engaging surface.

28. The hair removal device of claim 27, wherein:
(a) the support element is a removable plug through which high frequency energy waves are passed.

29. The hair removal device as set forth in claim 27, wherein:
(a) a reciprocable mounted button is disposed above the arm and when pressed comes in contact therewith to move the hair engaging surfaces into engagement with each other.

30. A hair removal device, comprising:
a support having a set of relatively movable hair gripping members mounted thereon
(b) each member having a conductive hair engaging surface adjacent but insulatively spaced from the periphery thereof, the surfaces being disposed in opposition to engage each other upon movement of the gripping members
(c) an insulated high frequency energy wave conductive path disposed between the support and one of the hair engaging surfaces, and
(d) a housing having support means for removably supporting the support and transmitting high frequency energy waves therethrough to said one of the hair engaging surfaces.

31. The hair removal device as set forth in claim 30, wherein:
(a) the support means for the gripping members is a socket having a pin connecting terminal for transmitting high frequency energy waves to one of the gripping members.

32. The hair removal device as set forth in claim 30, wherein:
(a) the housing is an elongated hollow member of insulative material which has a removable front section through which the gripping members extend.

33. An epilator arm for a hair removal device, comprising:
(a) a movable arm having a slender tip (b) a conductive hair engaging surface on the tip adjacent and spaced from the periphery of the tip (c) the tip shaped to preclude arcing to the skin (d) a conductor electrically connected to the hair engaging surface disposed within the movable arm and having high frequency energy wave insulation associated therewith (e) the periphery of the hair engaging surface being disposed approximately one thirty-second of an inch from the periphery of the tip, and (f) high frequency energy wave insulation disposed between the periphery of the tip and the periphery of the hair engaging surface.

34. The epilator arm for the hair removal device as set forth in claim 33, wherein:

(a) the tip in a plane perpendicular to the hair engaging surface has no less than one-sixteenth of an inch radius.

35. The epilator arm for the hair removal device as set forth in claim 33, wherein:

(a) the area of hair engaging surface is from one-fiftieth to one five-hundredth of an inch in area.

36. The epilator arm for the hair removal device as set forth in claim 35, wherein:

(a) the hair engaging surface has a dimension of approximately one-sixteenth of an inch by one-eighth of an inch.

37. An improved hand-held epilation unit of the type in which two opposed arms of a tweezer-like device are used to grasp a hair and through one of which radio frequency energy is supplied to the hair, wherein the improvement comprises:

(a) radio frequency focusing means on the arms for directing the radio frequency energy to and across the hair such that it then travels internally along the hair shaft down to the papilla area.

38. The improved epilation unit of claim 37, wherein the focusing means includes:

(a) relatively small conductor surfaces on each arm disposed in opposition to each other and which contact and grasp the hair between them (b) one of the surfaces connected to a radio frequency source, and (c) the conductor surfaces being fully enclosed by a radio frequency insulation material when they are brought together to grasp the hair.

39. The improved hand-held epilation unit of claim 38, wherein the focusing means includes:

(a) the radio frequency insulation material surrounding each of the conductor surfaces match and tightly contact each other when the opposed conductor surfaces are brought together.

40. The improved hand-held epilation unit of claim 38, wherein the focusing means includes:

(a) insulation material being disposed about the conductor surfaces which has a minimum thickness of approximately one thirty-second of an inch.

41. The improved hand-held epilation unit of claim 37, wherein the focusing means includes:

(a) two relatively small and flat conductor areas which are substantially flush with and surrounded by radio frequency insulator material, such that the surfaces close together in a sealing relationship and the radio frequency energy is directed across the hair.

* * * * *